United States Patent [19]
Utne et al.

[11] 3,992,459

[45] Nov. 16, 1976

[54] PREPARATION OF BIPHENYL COMPOUNDS

[75] Inventors: Torleif Utne, Warren; Ronald B. Jobson, Old Bridge; Alfred V. Lovell, Scotch Plains, all of N.J.

[73] Assignee: Merck & Co., Inc., Rahway, N.J.

[22] Filed: May 1, 1975

[21] Appl. No.: 571,165

[52] U.S. Cl. .......................... 260/649 F; 260/469; 260/612 R; 260/620; 260/647 DP
[51] Int. Cl.² ..................................... C07C 25/18
[58] Field of Search ...... 260/649 DP, 649 F, 613 R, 260/620, 679 R, 469, 612 R

[56] References Cited
FOREIGN PATENTS OR APPLICATIONS
211,921  1/1941  Switzerland .................. 260/649 DP

OTHER PUBLICATIONS

Merck Index p. 1205 (eighth ed.), 1968.

*Primary Examiner*—D. Horwitz
*Attorney, Agent, or Firm*—Harry E. Westlake, Jr.; William H. Nicholson; Frank M. Mahon

[57] ABSTRACT

Biaryl coupling, particularly to form 2,4-difluorobiphenyl, is accomplished by diazotizing an aniline and coupling the benzenediazonium salt with a second aromatic component in the presence of a strong acid, an inert finely divided solid and copper powder or a copper salt.

5 Claims, No Drawings

PREPARATION OF BIPHENYL COMPOUNDS

This invention is concerned with a novel process for biaryl coupling.

More particularly, it is concerned with the novel biaryl coupling reaction described by the following chemical representation:

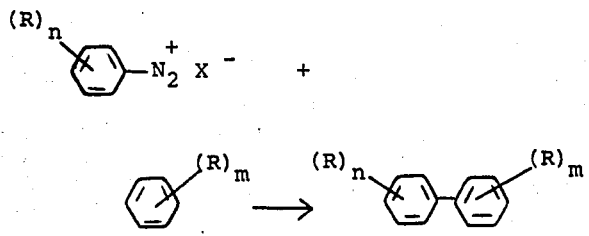

wherein the R groups are the same or different and each represents:
1. halo, such as chloro or fluoro,
2. hydroxy,
3. $C_{1-5}$ alkoxy,
4. $C_{1-5}$ alkoxycarbonyl;

$X^-$ is an acid anion, especially $BF_4^-$, or $CCl_3COO^-$;
$n$ is an integer from 0–2; and
$m$ is an integer from 0–2.

Even more particularly, this invention is concerned with the novel process represented above wherein $n$ is 2 and the R groups of that ring are both fluoro, and $m$ is zero.

The novel process of this invention is useful for the preparation of assymetric biaryl compounds, but especially in the preparation of 5-(2,4-difluorobenzene)-salicylic acid either directly by condensing a 2,4-difluororbenzenediazonium salt with a $C_{1-3}$ alkyl salicylate or indirectly by condensing a 2,4-difluorobenzenediazonium salt with benzene to produce 2,4-difluorobiphenyl. This latter compound is an intermediate in a potentially important process for preparing 5-(2,4-difluorobenzene)salicylic acid, a potent analgesic, antipyretic and antiinflammatory agent. This potentially important process is represented as follows:

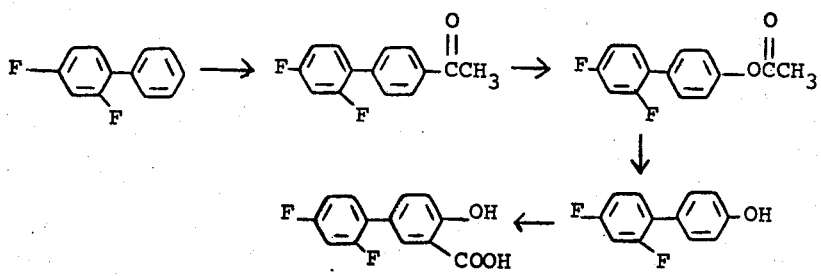

and is described and claimed by Jones et al., in U.S. Pat. application, Ser. No. 490,620, filed July 22, 1974 now abandoned. This process is as follows.

5-(2,4-Difluorophenyl)salicylic Acid

Step A: Preparation of 2,4-difluorobiphenyl

To a 50 liter resin pot equipped with stirrer, thermometer, nitrogen-inlet, internal steam coil and reflux condenser is charged 31.5 liters of benzene, 1.025 liters of isoamyl nitrite and 700 g. (5.43 moles) of 2,4-difluoroaniline.

The reaction mixture is heated to reflux. Vigorous nitrogen evolution begins at 70° C. Reflux begins at 74° and rises to 77° during the reaction period. The batch is refluxed for 5 hours. The benzene is atmospherically distilled (required 3.5 hours) and the residue is steam distilled until a single-phase distillate is collected (required 10 hours). The layers are separated and the aqueous portion is extracted with 2 × 2.6 liters of benzene. The combined benzene extracts are washed with 2 × 2.6 liters of water, dried over anhydrous magnesium sulfate and filtered. This dried benzene layer is combined with that from an identical run and the benzene is removed in vacuo. The residue, crude 2,54-difluorobiphenyl, weighed 1.321 kg. This crude is dissolved in a mixture of 4.4 liters isopropanol and 2.2 liters of water at 65°. The solution is cooled slowly to 25°, seeding during the cooling period, and aged at 25° for 1 hour. The batch is cooled to 0°–5°, aged at 0°–5° for 1 hour, and the solids are filtered, washed with 3 × 360 ml. of cold (0°) isopropanol/water (2/1) and then slurry-washed with 3.6 liters of water. The cake is air dried. Yield, 1.092 kg. (52.5%), m.p. 61°–63°.

Step B: Preparation of 4-2,4-difluorophenyl)acetophenone

Into a 12 liter round bottom flask, fitted with stirrer, thermometer, reflux condenser, addition funnel and nitrogen-inlet is charged 1.27 kg. (9.55 moles) of anhydrous aluminum chloride to 3.1 liters of methylene chloride. To this mixture is added 449 ml. (485 g.; 4.75 moles) of acetic anhydride at 15°–20° over a 20 minute period. To the resulting stirred solution is added 745 g. (395 moles) of 2,4-difluorobiphenyl in 1.88 liters of methylene chloride at 20°–25° over 45 minutes. The reaction is complete after 2.5 hours at 25° and the batch is quenched into 18.8 liters of ice and water. The layers are separated and the aqueous portion extracted with 2 × 6.2 liters of methylene chloride. The combined methylene chloride layers are washed with 3.4 liters of water, 6.2 liters of 20% aqueous sodium carbonate solution and 3.4 liters of water. After drying over anhydrous magnesium sulfate and filtering, the methylene chloride is removed in vacuo. Yield, 895.5 g. (98.5%); m.p. 78°–79°.

Step C: Preparation of 4-(2,4-difluorophenyl)phenylacetate

A 1.0 liter, three-necked round-bottom flask was fitted with stirrer, thermometer, reflux condenser and addition funnel. Fifty grams (50 g.; 0.216 mole) of 4-(2',4'-difluorophenyl)acetophenone, 92.2 g. (0.94 moles) of maleic anhydride, 198 ml. of methylene chloride and 48.7 ml. of glacial acetic acid were charged to the flask and heated to reflux (52°). A cold 50% aqueous hydrogen peroxide solution (22.2 g.; 0.326 moles as peroxide) was added, dropwise, over 30 minutes at reflux temperature. The batch was refluxed for an additional 7 hours, then cooled to 25°.

Solid sodium bisulfite (24.0 g.; 0.231 mole) was added to the batch, followed by 4.5 ml. of water. After stirring for 15 minutes at 25°, anhydrous sodium sulfate (7.5 g.) was added and the batch stirred for 2 hours at 25°. The solids were filtered and washed with 4 × 35 ml. of methylene chloride The combined filtrate and washes were concentrated in vacuo to dryness, flushed once with 75 ml. of isopropanol and again taken to dryness in vacuo (75 g.). This crude was recrystallized from 105 ml. of hot (80° C.) isopropanol. The clear solution was cooled to 0° and aged at 0° for 2 hours. The product was filtered, washed twice with mother liquors, then with 3 × 10 ml. of cold (0° C.) isopropanol and dried in vacuo at 50°. Yield, 48.7 g. (91%); m.p. 104°–107° C.

Step D: Prepration of 4-(2,4-difluorophenyl)phenol

A 30 liter resin pot is fitted with stirrer, thermometer and reflux condenser, and charged with 2.62 kg of 50% aqueous sodium hydroxide and 11.34 liters of water. 4-(2′,4′-Difluorophenyl)phenylacetate (1.876 kg., 7.55 m) is added and the batch is heated to reflux over 2.5 hours. The batch is refluxed for 2 hours (in solution at 75°), then cooled to 100° and added to a solution of 3.27 liters of concentrated hydrochloric acid in 9.8 liters of water in a 50 liter resin pot over a 30 minute period.

The termperature of the acid mixture rises to 40° during the addition. The batch is cooled to 20°, filtered on a 2 inch pot (paper and cloth) and washed with 4 × 4.06 liters of water. The batch is air-dried at 80°. Yield, 1.512 kg. (97.5%); m.p. 152°–154°. K.F. 0.12%.

Step E: Preparation of 5-(2,4-difluorophenyl)salicylic Acid

Anhydrous potassium carbonate (7.2 kg.; 52.0 moles) and 1.402 kg. (6.8 moles) of 4-(2′,4′-difluorophenyl)-phenol are blended in a mill and charged to a 5 gal. autoclave which is previously pressure-tested to 1900 p.s.i. with nitrogen. The autoclave is pressurized to 890 p.s.i. with $CO_2$ and the agitator is started. The batch is heated to 240° (2.25 hours heat-up time) and aged at 236°–246° for 6 hours. The reactions mixture is allowed to cool overnight and the autoclave is carefully vented. The solids are removed (weight of solids, 8.855 kg.) and transferred to a 20–30 gal. portable extractor. Add 5.5 gal. of water, agitate 15 minutes at 20°–25° and filter on a 19 inch pot set with cloth, paper and cloth. The cake is sucked to damp-dry and charged to a 100 ga. still with 37 gal. of water. The batch is heated to 80° (steam) and then 69.5 g. of tetrasodium versenate and 116 g. of Nuchar C-190N are added. Continue heating to 90° and filter through a Sparkler set with cloth, paper and cloth and pre-coated with Supercel. The Sparkler is washed with 3 × 4 gal. of 60°–70° water. The filtrate and washes are recharged to the clean still and the batch is acidified with 550 ml. of concentrated sulfuric acid (pH 2). The slurry is aged for 10 minutes and cooled to 25°. The solids are filtered on a 19 inch pot (cloth, paper, cloth), washed with 4 × 2 liters of water and dried in vacuo at 70° untl K.F. 1.0%. Yield, 1.507 kg. (88.5%, crude); m.p. 210°–212°.

A 50 liter resin pot is fitted with stirrer, thermometer, and steam coil and charged with 728.5 g of crude 5-(2,4-difluorophenyl)salicylic acid. Toluene (34 liters) is added and the batch is heated to effect solution (104°–108°). The batch is filtered through an 8 inch Sparkler filter.

A second, identical batch is processed in the same manner through the Sparkler filter and the Sparkler is washed with 5 gal. of hot toluene.

The combined filtrates are refrigerated over the weekend and filtered on a 20 inch pot set with cloth and paper. The solids are washed with one gallon of cold toluene and sucked damp-dry on the pt. The cake is trayed and air dried to constant weight at 75°. The drying process is finished in vacuo at 75°–80°. Yield, 1.352 kg. (93% recovery); m.p. 212°–213°.

The best known biaryl coupling reaction is the Gomberg-Bachmann-Hey reaction and minor modifications thereof as taught in the aforementioned United States Patent Application. These reactions also proceed via a diazonium intermediate, but at neutral or alkaline pH through a predominantly, if not entirely, free radical mechanism. Consequently, they result in the formation of large amounts of dark polymeric tars which reduces the yield of desired product to about 50% or below and greatly complicates the isolation and purification thus increasing the cost of synthesis in manpower, materials, time, and yield, as well as in ecological problems.

The novel procedure of this invention is designed to favor a carbonium (carbenium)ionic mechanism by operating in an acidic environment in the presence of a finely divided solid and a copper or copper salt catalyst. By so doing, yields of 80–95% are realized and the product is isolable by simple concentration of the reaction mixture and optional washing and/or recrystallization.

The process comprises combining on a molar basis one part of diazonium salt, 0–0.5 parts of a strong organic acid such as trichloroacetic or trifluoroacetic acid, 0.1 2 parts of copper powder, a finely divided solid such as silica gel, diatomaceous earth (Super-Cel), crushed glass, alumina, crushed molecular sieves, magnesium sulfate, or the like, in an excess of the second aryl component such as benzene, methyl salicylate, anisole, etc., which also acts as solvent for the reaction. The reaction is conducted at 5° C. to reflux temperature for 1–20 hours depending on the temperature.

The diazonium salt starting material for the above novel process can be prepared in a separate step and isolated in a pure state or, alternatively, it can be prepared in situ in the novel coupling procedure.

The preparation and isolation of the diazonium salt comprises: (1) dissolving the aniline starting material, such as 2,3-difluoroaniline in tetrahydrofuran or a lower alkanol, such as ethanol, propanol, or isopropanol; (2) adding to the solution at −5° to +10° C. from 1–3 molar equivalents of fluoboric acid; (3) mixing the resulting solution with 1–3 molar equivalents of a $C_{2-6}$ alkylnitrite, such as isopropyl nitrite or isoamyl nitrite or an alkali metal nitrite such as sodium nitrite in aqueous solution while maintaining the temperature at −5° to 15° C.; and (4) collecting the precipitate of the arylidazonium fluoborate, such as 2,4-difluorobenzenediazonium fluoborate. These diazonium salts are fairly unstable in the presence of hydroxylic solvents such as water and alcohols. Therefore, they are usually washed well with an alcohol such as isopropanol and a second solvent capable of removing the residual alcoholic solvents, such as ether or methylene chloride. The dry diazonium salt is stable if kept in a dry, cool, dark environment.

In the alternative procedure involving in situ preparation of the diazonium salt, the novel process is modified by the use of one part of an aniline in place of the described diazonium salt, and employing 1.1–1.5 parts of a strong organic acid as previously described, as well as a nitrosating agent such as isopropyl nitrite.

Example 1

2,4-Difluorobiphenyl

Step A: Preparation of 2,4-difluorobenzenediazonium Fluoborate

| | |
|---|---|
| 100 g. (0.78 mole) | 2,4-difluoroaniline (98%) |
| 1250 ml. | isopropanol |
| 250 ml. (1.86 moles) | fluoboric acid (48%) |
| 250 ml. (1.86 moles) | isoamyl nitrite |
| 500 ml. | ethyl ether |

A solution of 100 g. of 2,4-difluoroaniline in 250 ml. of isopropanol was chilled to 0° and 250 ml. of 48% fluoboric acid was added (exotherm to 20°). After cooling to −5° C., 250 ml. of isoamyl nitrite was added in a stream with vigorous stirring while keeping the temperature at 5° to 10° C. A thick precipitate rapidly formed. The mixture was diluted with 500 ml. of isopropanol and stirred at −5° C. for ten minutes. The precipitate was filtered off, washed well with 500 ml. of cold isopropanol, then with 500ml. of ether and vacuum dried at room temperature to yield 172 g. (98%) of white, crystalline, pure 2,4-difluorobenzenediazonium fluoborate, m.p. 147°–150° C., dec. 220°.

Step B: Preparation of 2,4-difluorobiphenyl

| | |
|---|---|
| 100 g. (0.44 mole) | 2,4-difluorobenzenediazonium fluoborate |
| 3 l. | benzene |
| 200 g. | silica gel, 60-200 mesh |
| 200 g. | copper powder |

2,4-Difluorobenzenediazonium fluoborate, 100 g., was slurried in 2.5 l. of benzene and 200 g. of silica gel and 200 g. of copper powder was added. The mixture was stirred vigorously at room temperature overnight, during which a slow but steady evolution of nitrogen was observed. The mixture was filtered and the copper/silica cake washed with 500 ml. of benzene. The combined filtrates were washed to neutrality with water, dried over sodium sulfate and concentrated to dryness to yield 66 g. (79%) of 2,4-difluorobiphenyl, m.p. 59°–61°, purity 97% by g.l.c.

Example 2

2,4-Difluorobenzenediazonium Fluoborate

| | |
|---|---|
| 13 g. (0.1 mole) | 2,4-difluoroaniline (98%) |
| 190 ml. | isopropanol |
| 30 ml. (0.22 mole) | fluoboric acid (48%) |
| 9 g. (0.13 mole) | sodium nitrite |
| 20 ml. | water |
| 100 ml. | ethyl ether |

A solution of 13 g of 2,4-difluoroaniline in 30 ml. of isopropanol was chilled to 0° and 30 ml. of fluoboric acid (48%) was added. After cooling to 0°, 9 g. of sodium nitrite in 20 ml. of water was added in a steady stream, with vigorous stirring, keeping the temperature at 5°–10° C. A thick precipitate rapidly formed, the mixture was diluted with 60 ml. of isopropanol and stirred at 0°–5° for 10 min. The precipitate was filtered off, washed well with 100 ml. of cold isopropanol, then with 100 ml. of ether and vacuum dried to yield 20 g. (88%) of white, crystalline 2,4-difluorobenzenediazonium fluoborate, m.p. 147°–150° C., dec. 220°.

Example 3

2,4-Difluorobenzenediazonium Fluoborate

| | |
|---|---|
| 13 g. (0.1 mole) | 2,4-difluoroaniline (98%) |
| 190 ml. | isopropanol |
| 30 ml. (0.22 mole) | fluoboric acid (48%) |
| 12 g. (0.16 mole) | dinitrogen trioxide |
| 100 ml. | ethyl ether |

A solution of 13 g. of 2,4-difluoroaniline in 100 ml. of isopropanol was chilled to 0° and 30 ml. of fluoboric acid (48%) was added. After recooling to 0°, dinitrogen trioxide gas was bubbled in at 0°–5° C. for 5 min., or until a positive potassium iodide/starch test was maintained. The product precipitated slowly. The mixture was stirred at 0°–5° for 30 min., filtered and the cake washed well with 100 ml. of cold isopropanol, then with 100 ml. of ether and vacuum dried to yield 20.5 g. (90%) of white, crystalline pure 2,4-difluorobenzenediazonium fluoborate, m.p. 147°–150° C., dec. 220°.

Example 4

2,4-Difluorobiphenyl

Step A: Preparation of 2,4-difluorobenzenediazonium Fluoborate

| | |
|---|---|
| 129 g. (1.0 mole) | 2,4-difluoroaniline (98% pure) |
| 400 ml. | isopropanol |
| 200 ml. (1.47 moles) | fluoboric acid (48%) |
| 180 g. (2.0 moles) | isopropyl nitrite |
| 200 ml. | methylene chloride |

A stirred solution of 129 g. of 2,4-difluoroaniline in 120 ml. of isopropanol was chilled to 0° and to 200°ml. of 48% fluoboric acid was added dropwise (exotherm to 20°). After cooling to 10°, this solution was added dropwise with stirring to a chilled (5°) solution of 180 g. of isopropyl nitrite in 100 ml. of isopropanol, keeping the temperature at about 5°–10°. A thick precipitate rapidly formed, accompanied by a considerable heat of crystallization, which was controlled by external cooling. The crystalline product was filtered off, washed well with about 180 ml. of ice-cold isopropanol followed by about 2 × 100 ml. of methylene chloride to yield 211 g. (93%) of 2,4-difluorobenzenediazonium fluoborate (II), m.p. 145°–148°, dec. 220°.

Step B: Preparation of 2,4-difluorobiphenyl

| | |
|---|---|
| 100 g. (0.44 mole) | 2,4-difluorobenzenediazonium fluoborate (95% pure) |
| 1.8 l. | benzene |
| 100 g. | Super-Cel |
| 10 g. | copper powder |
| 25 g. | trichloroacetic acid |

2,4-Difluorobenzenediazonium fluoborate, 100 g., was slurried in 1.2 l. of benzene and 100 g. of Super-Cel, 25 g. of trichloroacetic acid and 10 g. of copper powder was added. The mixture was stirred vigorously at reflux temperature over four hours, during which a steady evolution of nitrogen and anhydrous fluoboric acid (or HF/BF$_3$) was observed. The mixture was filtered hot and the copper/Super-Cel cake washed with 3 × 200 ml. of benzene. The combined filtrates were washed to neutrality with water, dried over sodium sulfate and concentrated to dryness to yield 75 g. (89%) of 2,4-difluorobiphenyl, m.p. 58°–61°, purity 95% by quantitative glc.

Example 5

Preparation of 2,4-Difluorobiphenyl Involving in Situ Formation of Diazonium Salt

| | |
|---|---|
| 12.9 g. (0.10 mole) | 2,4-difluoroaniline (98%) |
| 14.0 g. (0.152 mole) | trichloroacetic acid |
| 25.0 g. (0.157 mole) | isopropyl nitrite |
| 2.0 g. (0.03 mole) | copper powder |
| 400 ml. | benzene |
| 40 g. | magnesium sulfate, anhydrous |
| 3 g. | charcoal |
| 5 g. | silica gel |
| 150 ml. | hexane |

To a stirred solution of 25.0 g. of trichloroacetic acid in 250 ml. of benzene was added 2.0 g. of copper powder and 20 g. of anhydrous magnesium sulfate, and the mixture cooled to +5° C. At this temperature, 14 g. of isopropyl nitrite was quickly added, immediately followed by the dropwise addition of a solution of 12.9 g. of 2,4-difluoroaniline in 100 ml. of benzene over about 20 min. The temperature was kept at 10°–15° C. throughout the addition, then gradually let warm to 25° C. After 1 to 1½ hours the nitrogen gas evolution subsided, the solids were filtered off, and the filtrate washed with water 5 × 500 ml. to neutrality. The organic layer was dried over 20 g. of magnesium sulfate, treated with 3 g. of charcoal, filtered and concentraed under vacuum to an oil. This oil was dissolved in 150 ml. of hexane and stirred with 5 g. of silica gel, which removed most of the color. Upon filtration, the pale yellow filtrate was concentrated under reduced pressure to give 17.5 g (91%) of off-white crystalline 2,4-difluorobiphenyl (II), m.p. 59.5°–63°., quant. vpc showing 95% purity. All physical data obtained confirmed the structure.

When in Example 5 the 2,4-difluoroaniline is replaced by aniline and the benzene is replace by m-difluorobenzene, a yield of about 70% of 2,4-difluorobiphenyl is obtained.

EXAMPLE 6

2,4-Difluoro-4'-methoxybiphenyl 2,4-Difluorobenzene diazonium fluoborate (22.7 g., 0.1 mole) was stirred at room temperature in 100 ml. of anisole to which was added 10 g. of copper powder and 10 g. of silica gel. the mixture was stirred vigorously in a water bath, the internal temperature rising exothermically to 40° C. while the nitrogen gas evolution ceased after about 2 hours. The reaction mixture was diluted with 100 ml. of chloroform, filtered and the filtrate washed with water to neutrality, dried and concentrated under vacuum to an oil. The crude oil was dissolved in 100 ml. of hot isopropanol, then chilled at 0°–5° C. with stirring for several hours. The crystaline product was collected, washed with cold isopropanol and air dried to yield 8.8 g. (40%) of 2,4-difluoro-2'-methoxybiphenyl as cream colored crystals, m.p. 85°–88° C. Concentration of the mother liquors yielded 4.4 g. (20%) of the 2,4-difluoro-4'-methoxybiphenyl as cream colored crystals, m.p. 73°–76°. The structures were confirmed by NMR, as well as by methylation of authentic phenolic material.

EXAMPLE 7

Methyl 5-(2,4-difluorobenzene)salicylate 2,4-Difluorobenzenediazonium fluoborae, (2.27 g. 0.01 mole) was stirred at room temperature in 25 ml. of methyl salicylate to which 2 g. of copper powder and 2 g. of silica gel was added. The mixture was stirred vigorously at room temperature overnight while a slow evolution of nitrogen gas was observed. The mixture was diluted with 50 ml. of chloroform and filtered, the filtrate washed to neutrality with water, dried and concentrated to a dark oil. Gas chromatograhy indicated that about 20% of biphenylic products had been formed consisting of four components, the two major of which were the 3'- and 4'- isomers of the desired product, in a ratio of 2:1. Mass spectrography comfirmed the identy of these products.

Alkylation of the phenolic hydroxyl of methyl salicylate with a n-butyl or s-butyl group improved the desired situation a little, to give a 1:1 ratio of the two isomers. Acetylation of the same phenolic group did not change the ratio at all, presumably because of cleavage to the free phenol by the boron trifluoride liberated.

EXAMPLE 8

Methyl 5-(2,4-difuorobenzene)salicylate

Methyl 5-aminosalicyl diazonium fluoborat (1 g., 3.8 mmole) was slurried in 10 ml. ($d_{20}$ = 1.15) of m-difluorobenzene to which 0.5 g. of trichloroacetic acid, 0.5 g. of copper powder and 1 g. of Supercel was added. The mixture was refluxed overnight, a slow nitrogen gas evolution being observed. The excess difluorobenzene was was distilled off at atmospheric pressure (recovery 8 ml. or 85%). The residue was treated with 20 ml. of methylenechloride and upon filtration about 0.5 g. (50%) of the diazonium fluoborate starting material was recovered. The combined filtrate and methylene chloride washings were washed to neutrality with water, dried over magnesium sulfate and concentrated under vacuum to give 0.3 g. of an oily product, which crystallized on standing. Vpc showed this material to be about 50% of the desired methyl ester, besides about 40% methyl salicylate, leaving an overall coupling yield of 30% if corrected for recovered diazonium fluoborate.

EXAMPLE 9

Methyl 5-(2,4-difluorobenzene)salicylate

To a stirred slurry of 2 g. (6 mmoles) of methyl 5-aminosalicylate trichloroacetate salt in 25 ml. of m-difluorobenzene was added 1 g. of magnesium sulfate and 1 g. of cupric trichloroacetate. The mixture was cooled to 0°–5° C. and 2 ml. of isopropyl nitrite added. The mixture was let warm to room temperature with stirring overnight. After refluxing for 3 hours, the excess m-difluorobenzene was removed (20 ml., 85% recovery) and the residue extracted with some chloroform. The extract was washed to neutrality with water, dried over magnesium sulfate and concentrated to a dark oil, weighing 1.5 g. Vpc showed this material to be 50% pure with respect to the desired ester, corresponding to a yield of 47% of the 5-aminosalicylate charged.

What is claimed is:

1. In a process comprising coupling of a benzene diazonium compound with benzene or substituted benzene in neutral or basic conditions by a substantially free radical mechanism, wherein the improvement comprises conducting the coupling in an acidic environment in the presence of a finely divided inert solid and copper powder, or copper salt, whereby an ionic mechanism prevails and the yield is increased by avoiding tar formation.

2. A process for the preparation of a compound of formula:

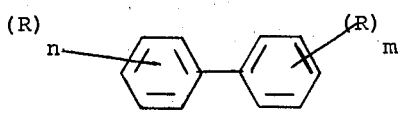

wherein the R groups can be the same or different and each is:
1. chloro or fluoro,
2. hydroxy,
3. $C_{1-5}$ alkoxy,
4. $C_{1-5}$ alkoxycarbonyl;

$n$ is 0–2; and
$m$ is 0–2;

which comprises reacting a compound of formula:

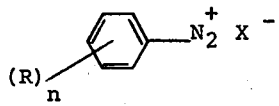

wherein $X^-$ is the anion of fluoboric acid or trichloroacetic acid, with a compound of formula:

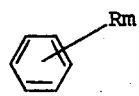

in the presence of a finely divided inert solid and copper powder or a copper salt and optionally a strong organic acid for 1–20 hours at +5° C. to reflux temperature.

3. The process of claim 2 for the preparation of 2,4-difluorobiphenyl which comprises reacting 2,4-difluorobenzenediazonium fluoborate with benzene.

4. The process of claim 2 for the preparation of 2,4-difluorobiphenyl which comprises reacting 2,4-difluorobenzenediazonium trichloroacetate with benzene.

5. The process of claim 2 for the preparation of 2,4-difluorobiphenyl comprising the coupling of 2,4-difluorobenzenediazonium fluoborate or 2,4-difluorobenzenediazonium trichloroacetate with benzene in an acidic environment in the presence of a finely divided inert solid and copper powder, or copper salt.

* * * * *